United States Patent
Pophillat et al.

(10) Patent No.: US 8,891,072 B2
(45) Date of Patent: Nov. 18, 2014

(54) SUPPORT, APPARATUS AND METHOD FOR PERFORMING A REFLECTION MEASUREMENT ON AN EYEGLASS

(71) Applicant: Essilor International Compagnie Generale d'Optique, Charenton le Pont (FR)

(72) Inventors: Olivier Pophillat, Charenton le Pont (FR); Stephane Gueu, Charenton le Pont (FR)

(73) Assignee: Essilor International (Compagnie Generale d'Optique), Charenton-le-Pont (FR)

( * ) Notice: Subject to any disclaimer, the term of this patent is extended or adjusted under 35 U.S.C. 154(b) by 0 days.

(21) Appl. No.: 14/210,744

(22) Filed: Mar. 14, 2014

(65) Prior Publication Data

US 2014/0192345 A1    Jul. 10, 2014

Related U.S. Application Data

(63) Continuation of application No. PCT/IB2012/003011, filed on Dec. 4, 2012.

(51) Int. Cl.
 *G01J 3/00* (2006.01)
 *G01N 21/00* (2006.01)
 *G02B 7/02* (2006.01)
 *G01N 21/01* (2006.01)
 *G01N 21/84* (2006.01)

(52) U.S. Cl.
 CPC ............... *G01N 21/84* (2013.01); *G01N 21/01* (2013.01)
 USPC .......... 356/51; 356/239.2; 451/364; 359/811; 359/818; 359/819; 359/822; 359/829

(58) Field of Classification Search
 CPC .............. G02C 1/02; G02C 1/08; G02C 5/16; G02C 5/2209; G02C 5/2227; G01M 11/0228; G01M 11/0214; G01M 11/02; G01M 11/0235; G01M 11/00; G01B 11/007; G01B 11/026
 USPC ........................................ 356/239.2; 451/364
 See application file for complete search history.

(56) References Cited

U.S. PATENT DOCUMENTS 3,242,581 A * 3/1966 Wagener ........................ 356/125
(Continued)

OTHER PUBLICATIONS

International Search Report dated Jun. 27, 2013, corresponding to PCT/IB2012/003011.
Measuring AR Performance and Layer Properties of Ophthalmic Lenses—with NKD Series; Jan. 1, 2008, pp. 1-4, XP055066769.
(Continued)

*Primary Examiner* — Tarifur Chowdhury
*Assistant Examiner* — Sunghee Y Gray
(74) *Attorney, Agent, or Firm* — Young & Thompson

(57) ABSTRACT

An eyeglass support is adapted for pinch-holding the eyeglass (5) between three first contact portions (41-43) and three second contact portions (61-63). The first contact portions form a height reference for positioning the eyeglass whereas the second contact portions ensure application of the eyeglass against the first contact portions while conforming to any possible shape for the eyeglass. The support suits for being incorporated in a reflection measurement apparatus. In particular, it is useful for measuring reflection of eyeglasses provided with antireflecting coatings or for rating a protection against UV hazards which is provided by an eyeglass to a wearer of the eyeglass.

20 Claims, 4 Drawing Sheets

(56) References Cited

U.S. PATENT DOCUMENTS

| | | | |
|---|---|---|---|
| 3,858,982 | A * | 1/1975 | Meckler ......................... 356/127 |
| 6,798,501 | B1 * | 9/2004 | Mizuno .......................... 356/124 |
| 2004/0234780 | A1 | 11/2004 | Koenig et al. |
| 2013/0235370 | A1 * | 9/2013 | Boutinon et al. ............. 356/124 |

OTHER PUBLICATIONS

Non-Destructive Quality Assurance with Spectral Measurement Assurance With Spectral Measurement of Curved Surfaces; Jan. 1, 2008; XP055066770.

Case Studies: "Complete Thin Film Measurement"; Jan. 1, 2008; p. 1; XP055068476.

* cited by examiner

SUPPORT, APPARATUS AND METHOD FOR PERFORMING A REFLECTION MEASUREMENT ON AN EYEGLASS

FIELD OF THE INVENTION

The invention relates to a support, an apparatus and a method for performing a reflection measurement on an eyeglass. In particular, the reflection measurement may be in the wavelength ranges of visible, UV A and UV B radiations.

Such measurement may be useful in particular for quantifying an antireflection efficiency of the eyeglass for visible radiations.

It may also be useful for quantifying a protection which is provided by the eyeglass to a wearer, against UV-hazards.

BACKGROUND OF THE INVENTION

Known optical analysis techniques such as reflectometry and ellipsometry involve reflection measurements. Also many apparatuses are commercially available for enabling these techniques.

But these apparatuses are designed for performing the reflection measurements on samples with planar reflecting faces. For example, the measured samples are silicon wafers provided with thin films as used for microelectronic applications. They may also be flat glass samples with coatings, for example in view of manufacturing architectural or automotive glazings, or also display panels.

However, reflection measurements performed on eyeglasses are required, in particular for quantifying a residual reflection of eyeglasses which are provided with antireflecting coatings, and for quantifying a protection efficiency which is provided to an eyeglass wearer against UV-radiation hazards. For eyeglasses with antireflecting coatings, the measurements deal with visible radiations, namely in the wavelength range comprised between 380 nm (nanometer) and 780 nm, and incidence angle values equal to or less than 17° (degree). For UV-protection rating, the measurements deal with UV-A and UV-B radiations, with wavelength values of between 280 nm and 380 nm, and incidence angle values such as 30° and even 45°.

But due to the curved shapes of eyeglass faces, either concave or convex, the currently available apparatuses do not allow performing reflection measurements on eyeglasses. Indeed, these apparatuses are not designed for exposing to a measurement light beam a face of a sample which is curved, and controlling a height of the sample face at the location of the measurement in this face. In addition, the curvature of the sample face causes errors in the measurement result if no attention is especially drawn on the optical consequences of the curvature of the measured face.

Starting from this existing situation, one object of the present invention is to allow reflection measurements for eyeglasses in a simple and efficient manner, and with high measurement accuracy.

Another object of the invention is to allow using one and same apparatus for quantifying the residual reflection of an eyeglass provided with an antireflecting coating effective in the visible wavelength range, but also for rating the UV-protection which is provided to an eyeglass wearer.

Still another object of the invention is to measure reflection on an eyeglass without damaging the eyeglass or requiring permanent alteration of the eyeglass.

SUMMARY OF THE INVENTION

To achieve at least one of these objects or others, the present invention proposes a novel support which is adapted for performing reflection measurements on an ophthalmic eyeglass. The support comprises:

an upper part, which comprises itself an upper base element and three first contact portions arranged rigidly on a lower end of the upper base element so as to produce respectively three first point-contacts with a first face of the eyeglass at respective reference locations which are fixedly defined with respect to the upper part;

a lower part, which comprises itself a lower base element and three second contact portions each mounted on the lower base element so as to extend from an upper end of this lower base element up to respective variable distances beyond the upper end of the lower base element, and capable of providing three second point-contacts; and means for retaining the upper and lower parts with their respective lower and upper ends facing one another, while pressing the second contact portions towards the upper part so that the eyeglass is held between the first contact portions and the second contact portions, with the three second point-contacts located in a second face of the eyeglass which is opposed to the first face.

Additionally, the upper base element has recesses provided in opposed side faces of this upper base element, so that a light beam which propagates in one of these recesses can impinge on the first face of the eyeglass at a measurement location situated between the three first point-contacts, and a reflection direction of the light beam from the measurement location in the eyeglass first face runs through the other one of the recesses and exits from this other recess.

Thus, with the invention support, the eyeglass is pinched between the upper and lower parts, so that the eyeglass holding can be simple, easy and fast to obtain. The contact portions of the upper part form a height reference for the measured eyeglass face, which is compatible with a curved shape of this face. Also the contact portions of the lower part of the support can conform to the shape of the other face of the eyeglass, whatever this other face. Thus, the invention support ensures that the reflection-measured face of the eyeglass correctly pushes against the contact portions of the upper part of the support. The height of the reflection-measured face is thus controlled accurately.

Preferred embodiments of the invention may implement the following improvements, separately or in combination of several of them:

the lower and upper parts may be oriented about an axis extending from the lower end of the upper base element towards the upper end of the lower base element, so that the three first point-contacts are respectively in line with the three second point-contacts along directions parallel to the axis. In this way, any deformation of the eyeglass which might be caused by pinching forces involved for holding the eyeglass can be avoided;

the recesses in the opposed side faces of the upper base element may be designed so that an incidence angle between a propagation direction of the impinging light beam and a direction perpendicular to a plane containing the three first point-contacts, is comprised between 15° and 45° included;

the lower base element may have a clearing recess provided in a side face of this lower base element, so that a portion of the light beam which is transmitted through the eyeglass when held between the first contact portions and the second contact portions, propagates through the clearing recess after exiting at the second face of the eyeglass;

the three first contact portions may be arranged at the lower end of the upper base element so that they form an equilateral triangle. The support can thus suit in an optimal manner to most of possible shapes for the first face of the eyeglass to be reflection-measured; and the means for retaining the upper and lower parts may comprise a lift system suitable for moving the lower part towards the upper part until the eyeglass is pinch-held between the three first contact portions and the three second contact portions, while limiting a pressure of the three first contact portions onto the first face of the eyeglass, and of the three second contact portions onto the second face of the eyeglass. Thus, the eyeglass faces are not damaged by the contact portions on either face, and the eyeglass can be installed in the invention support with a rapid and easy-to-implement operation.

The invention also proposes a reflection measurement apparatus which comprises a support as just described, possibly with the improvements just listed. The apparatus further comprises a light source, a light intensity sensor, a light delivery port and a light collecting port. The light delivery port is connected to the means for retaining the upper and lower parts so that a light beam which is produced by the light source exits through the light delivery port, then propagates through one of the recesses of the upper base element and impinges onto the first face of the eyeglass. The light collecting port is also connected to the means for retaining the upper and lower parts so that the beam produced by the light source and reflected by the first face of the eyeglass runs through the other recess of the upper base element, then enters into the light collecting port and reaches the light intensity sensor.

In some embodiments of the invention apparatus, the light source may be adapted for outputting the light beam with radiation continuously distributed over the wavelength range from 280 nm to 780 nm. Then, the apparatus may further comprise a radiation selector which is arranged so that the light intensity sensor senses radiations limitedly within a wavelength window selected between 280 nm and 780 nm.

The apparatus may also comprise an angle setting system which is adapted for moving both the light delivery port and the light collecting port so that the incidence angle of the impinging light beam and also existing between the direction perpendicular to the plane containing the three first point-contacts and the propagation direction of the light beam as reflected by the eyeglass first face, can be set to a target value. This target value may be selected within an angle range extending from a lower angle value which is less than or equal to 17°, up to an upper angle value which is higher than or equal to 45°.

Separately or in combination with the angle setting system, the apparatus may also comprise a transverse positioning system which is adapted for setting a transverse position of the eyeglass along directions perpendicular to the axis extending from the lower end of the upper base element towards the upper end of the lower base element. The measurement location can then be selected within the first face of the eyeglass by the setting of the transverse positioning system. This transverse positioning system may comprise at least one abutment segment which is arranged for contacting a peripheral edge of the eyeglass, and adjustable in a separating distance from the measurement location. The transverse positioning system may also comprise a setting device based on the diameter of the eyeglass, so that the measurement location can be identified by its separating distance from either a peripheral edge or a center point of the eyeglass.

The invention further proposes a method for performing a reflection measurement on an eyeglass, using an apparatus as described here-above, which method comprises the following steps:

/1/ providing a set of reference samples having respective measurement faces of spherical shapes with known curvature values, each reference sample having a known reflection value and being designed so that a back face of this reference sample does not contribute to reflecting radiation;

/2/ obtaining the eyeglass to be reflection-measured, and also a mean curvature value of a face of this eyeglass where the reflection measurement is to be performed;

/3/ selecting one of the reference samples, so that the curvature value of the selected reference sample matches the mean curvature value of the eyeglass face to be reflection-measured;

/4/ using the apparatus with the selected reference sample held in the support, performing a first reflection measurement and obtaining a first intensity value from the light intensity sensor;

/5/ replacing the reference sample with the eyeglass in the support, and performing a second reflection measurement and obtaining a second intensity value from the light intensity sensor; and /6/ obtaining a result for the reflection value of the eyeglass face by combining the reflection value of the reference sample selected in step /3/, with the first and second intensity values respectively obtained in steps /4/ and /5/.

In the invention method, the known reflection values of the reference samples and the measurements which are performed in steps /4/ and /5/ relate to one and same incidence angle value and one and same wavelength window. Such method suits for measuring reflection for samples with curved light-reflecting faces such as eyeglasses, without the measurement results being corrupted by the curvatures of the measured faces.

BRIEF DESCRIPTION OF THE DRAWINGS

For clarity sake, the elements represented in these figures may not be sized in relation with actual dimensions, nor with ratios of actual dimensions. In addition, same reference numbers which are used in different figures denote same elements.

DETAILED DESCRIPTION OF THE INVENTION

Figure 1:
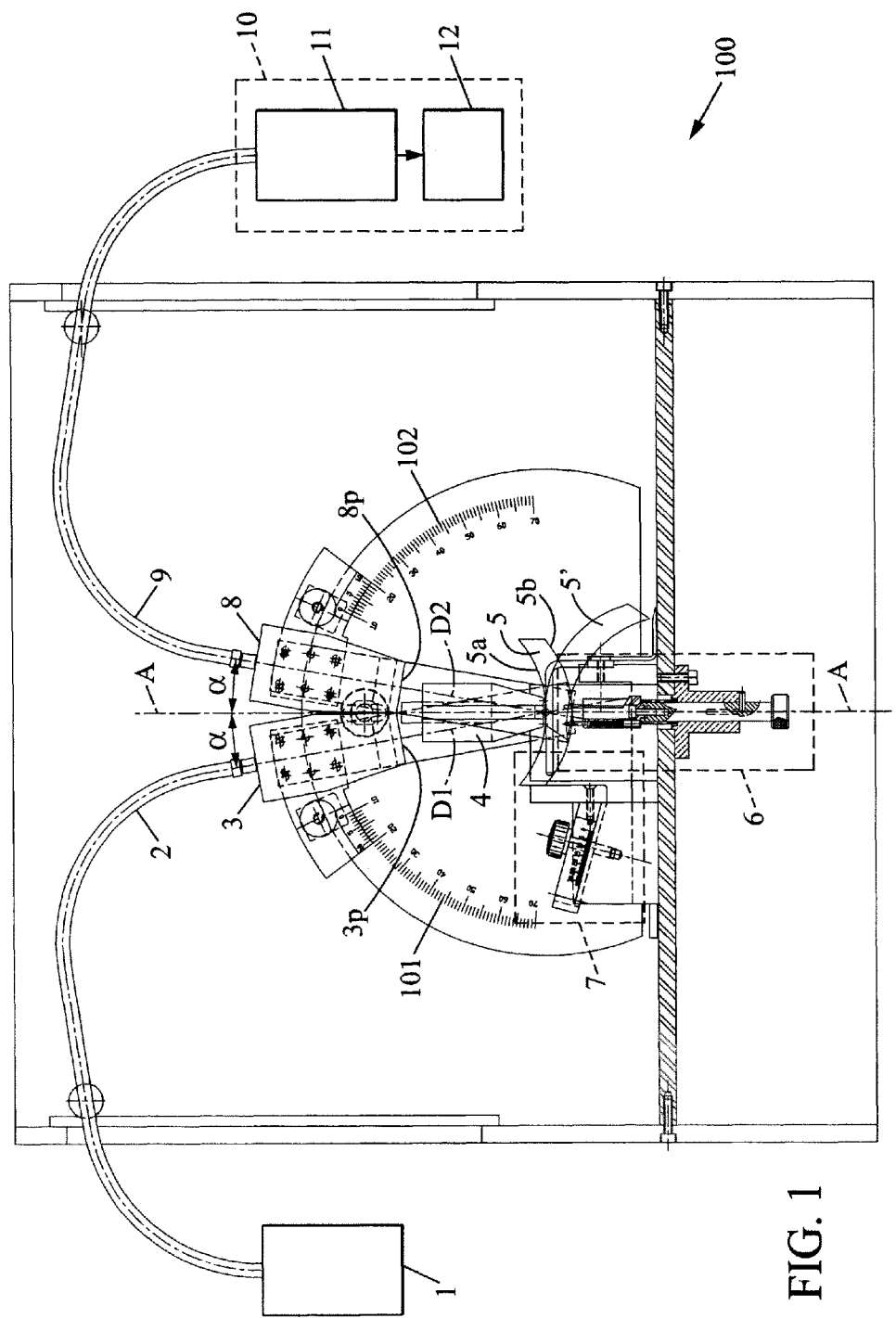
FIG. 1 is a general front view of a reflection measurement apparatus according to the invention.

According to FIG. 1, a reflection measurement apparatus which is generally denoted 100 comprises:
a light source 1,
a light delivery head 3, with light delivery port 3p,
a first optical fiber 2 for conducting a light beam produced by the light source 1 to the light delivery head 3,
a light collecting head 8, with light collecting port 8p, a second optical fiber 9 for conducting light collected by the light collecting head 8 towards a light intensity sensor, optionally, a radiation selector 11 designed for selecting in the light collected, radiations with wavelength contained in a desired wavelength window, and the light intensity sensor 12.

Reference number 5 denotes an eyeglass to be reflection-measured, with upper optical face 5a and lower optical face 5b. The eyeglass face 5a is that to be reflection-measured. For example, the eyeglass face 5a is concave and the eyeglass face 5b is concave. Then, the light beam output by the light delivery port 3p is directed onto the eyeglass face 5a, and a reflected portion of this light beam enters into the light collecting port 8p. Reference number 5' denotes another positioning of the eyeglass 5 in the apparatus 100, such that the reflection measurement is performed on the convex one of its optical faces. D1 denotes the propagation direction of the light beam output by the light delivery head 3, and D2 denotes the propagation direction of the reflected portion of the light beam, towards the light collecting head 8.

A-A denotes an axis of the apparatus 100, which is intended to be perpendicular to the face 5a of the eyeglass 5 at the measurement location. Thus, directions D1 and D2 are symmetrical with respect to the axis A-A, with an incidence angle α existing between the axis A-A and the direction D1. The angle α is also the reflection angle which exists between the axis A-A and the direction D2. The angle rules 101 and 102 are designed for allowing adjustment of the incidence angle α for the head 3 and for the head 8, in order to collect the reflected beam portion. For example, the apparatus 100 is designed for allowing the incidence angle α to be set at values ranging from 10° to 70°.

The support of the eyeglass 5 comprises itself an upper part 4, a lower part 6, and a base part for retaining the upper part 4 and the lower part 6 with respect to the other components of the apparatus 100. Actually, the base part may be integral with a supporting frame of the whole apparatus 100. Preferably, the base part retains the support upper part 4 rigidly with respect to the supporting frame.

Reference number 7 denotes an additional system for adjusting a position of the eyeglass 5 along directions perpendicular to the axis A-A. System 7 will be described later below.

The light source 1 may be of any type suitable for measurements within the desired wavelength range. For example, a combination of a deuterium lamp and a tungsten lamp is suitable for measurements in the wavelength range from 280 nm to 780 nm, corresponding to UV-B, UV-A and visible radiations.

The light delivery head 3 and the light collecting head 8 may each have any optical structure suitable for adapting the light beam in cross-sectional profile between the corresponding fiber 2 or 9 and the measurement location on the face 5a of the eyeglass 5. For example, each head 3, 8 may comprise two lenses selected for producing the light beam with a 2 mm cross-sectional diameter at the measurement location.

The radiation selector 11 and the light intensity sensor 12 may be comprised within a spectrophotometer 10 of any type commercially available.

Figure 2A:
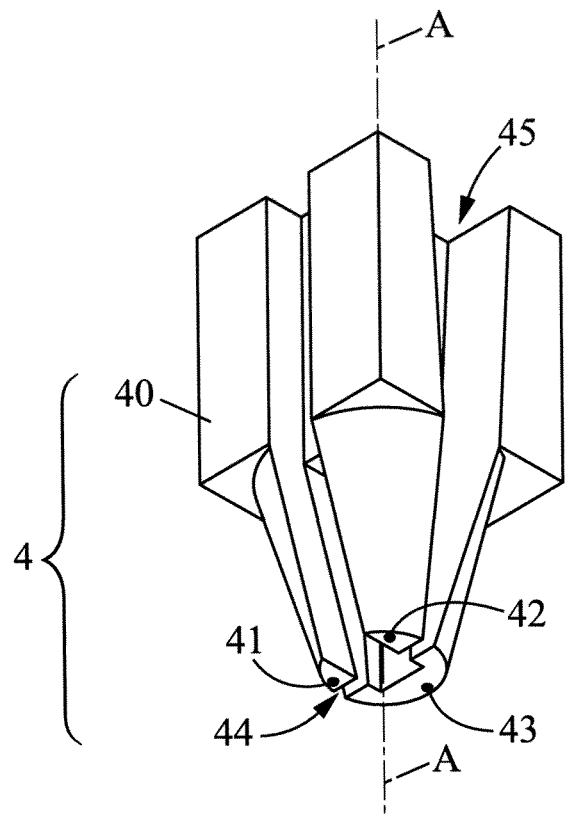
FIGS. 2a and 2b are respectively a perspective view and a top view of an upper part of an eyeglass support according to the invention, as used in an apparatus according to FIG. 1.
Figure 2B:
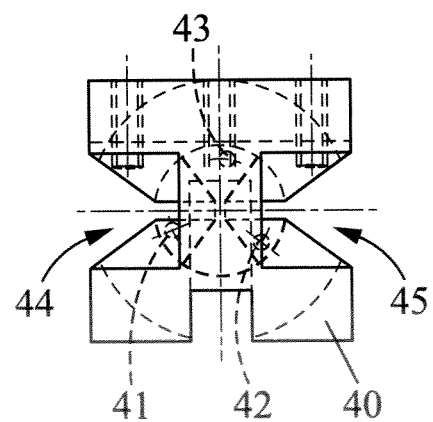

According to FIGS. 2a and 2b, the upper part 4 of the support comprises an upper base element 40 and three contact portions 41, 42 and 43. The portions 41 to 43 may each be comprised of a rod mounted fixedly in the base element 40, with the free end of the rod of spherical shape and extending from a lower face of the base element 40. The base element 40 is rigidly maintained in the apparatus 100, for example with the contact portions 41 to 43 oriented downwards. The rods of the contact portions 41 to 43 are parallel and extend down to a common height in projection on the axis A-A. The extension length of each rod out of the base element 40 may be comprised between about 1.2 mm (millimeter) and 3 mm. Additionally, the contact portions 41 to 43 may be distributed in the lower face of the base element 40 so as to form an equilateral triangle, for example with 10.8 mm in side length, and centered with respect to the axis A-A.

Figure 3:
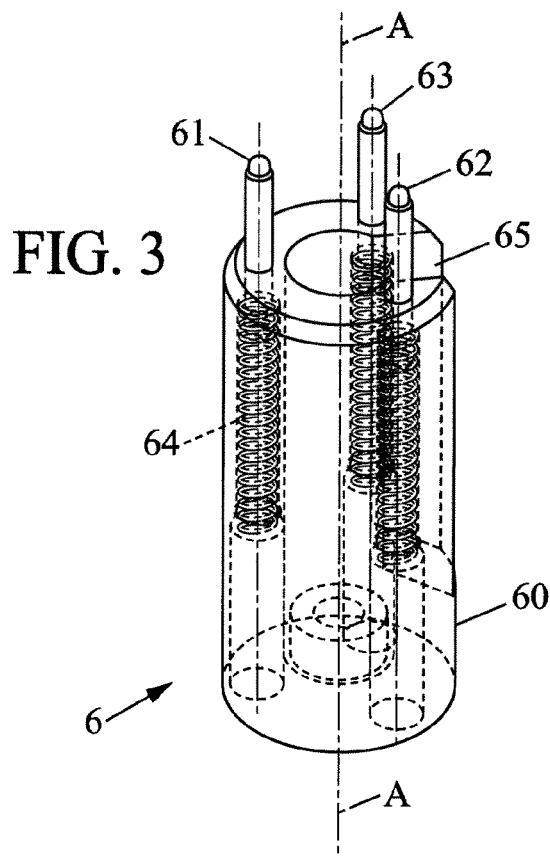
FIG. 3 is a perspective view of a lower part of the eyeglass support according to the invention.

According to FIG. 3, the lower part 6 of the eyeglass support is comprised of a lower base element 60 which is provided with three retractable fingers 61, 62 and 63 identical to each other and oriented upwards. Each of the fingers 61 to 63 is comprised of a rigid rod extending out from an upper face of the lower base element 60, parallel to the axis A-A, but with a protrusion length variable due to a spring 64 mounted between the rod and the lower base element 60. Preferably, the fingers 61 to 63 are respectively arranged in the upper face of the lower base element 60 in line with the contact portions 41 to 43, along directions parallel to the axis A-A. The upper ends of the rods which form the fingers 61 to 63 may also be shaped as half-spheres for forming additional contact portions.

Figure 4:
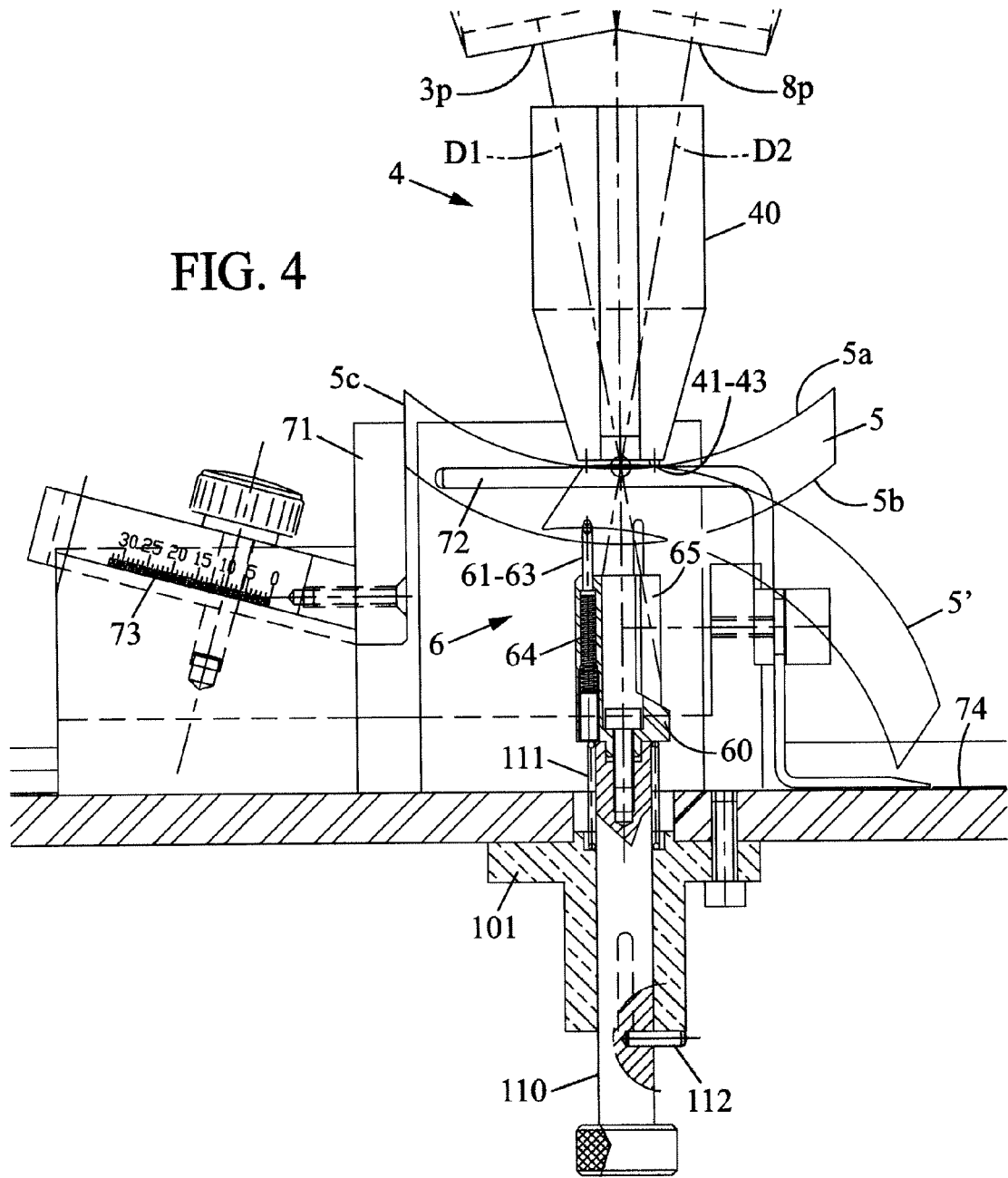
FIG. 4 is an enlarged view of the center part of the apparatus of FIG. 1.

The lower base element 60 of the support may be mounted on a lift system movable with respect to the apparatus 100 (FIG. 4). For example, the lift system may be comprised of a solid member 110 of cylinder shape oriented along the axis A-A, so that it can slide through a bottom part 101 of the apparatus 100. A spring 111 pushes the member 110 together with the lower part 6 of the support upwards until a stop element 112 abuts against the bottom part 101 for avoiding that the lower part 6 knocks against the upper part 4.

Hence, the eyeglass 5 can be inserted between the upper part 4 and the lower part 6 by pulling downwards the lift system, and then letting the spring 111 pressing the lower base element 60 upwards. The eyeglass 5 is thus pinched with the portions 41 to 43 contacting its upper face 5a, and the fingers 61 to 63 contacting the eyeglass lower face 5b. All contacts are point-contacts but soft enough not to scratch the eyeglass faces 5a and 5b. Preferably each spring 64 is about one third in stiffness as compared to the spring 111 of the lift system. In this way, the eyeglass 5 can be held in the apparatus 100 so as to arrange any location within the face 5a on the axis A-A, provided that the contact portions 41 to 43 and the fingers 61 to 63 are situated within the peripheral edge 5c of the eyeglass 5 (see FIG. 5). Then, the reflection measurement will be carried out at this location.

Because the contact portions 41 to 43 are close to each other, the height of the eyeglass face 5a is almost constant between these contact portions despite the curvature of the face 5a. This height is accurately controlled by the positioning of the upper base element 40 along the axis A-A. It is set so that the light beam output by the light delivery head 3 is reflected by the face 5a, and the reflected beam enters into the light collecting port 8p, whatever the incidence angle α. The upper base element 40 is further provided with two recesses 44 and 45, suitable for avoiding that the incident light beam and the reflected light beam are hindered by the upper base element 40 itself, for any value of the incidence angle α. The recesses 44 and 45 may be grooves machined in the opposed side faces of the upper base element 40. Because of the difference in height along the axis A-A between both faces 5a and 5b of the eyeglass 5, and also because of a possible non-zero prism existing between both faces 5a and 5b at the measurement location, an additional beam portion which is reflected upwards by the face 5b does not enter into the light collecting port 8b, so that it does not participate to the measured value for the reflection.

In addition, any method for suppressing or discarding the portion of the light beam which is transmitted through the eyeglass 5 may be implemented. Such suppression of the light transmitted through the eyeglass 5 may participate to improving the accuracy of the reflection measurements. This may be important in particular for low intensity of the reflected beam, for example when the face 5a of the eyeglass 5 is provided with an antireflecting coating. To this purpose, a clearing recess 65 (see FIGS. 3 and 4) may be provided in the lower base element 60, at its side face which is opposed from the side of the impinging light beam. The recess 65 may be a groove machined in the lower base element 60, from its upper face and side face towards the axis A-A. In this way, the portion of the light beam which is transmitted through the eyeglass 5 and exits at its second face 5b can propagate through the recess 65 until its is trapped, reflected away of discarded using any suitable manner.

Figure 5:
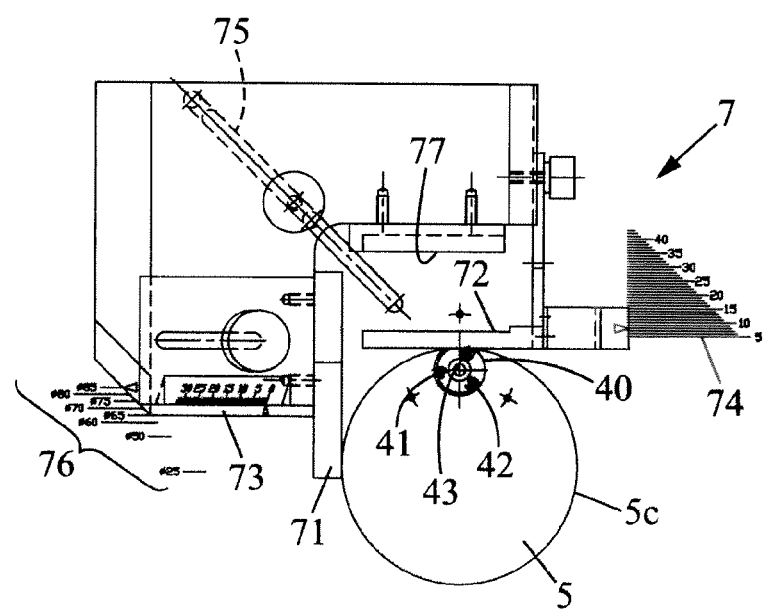
FIG. 5 is a top view of a transverse positioning device implemented in the apparatus of FIG. 1.

The transverse positioning system 7 allows selecting the measurement location within the eyeglass face 5a. As shown by FIG. 5, the system 7 may comprise two abutment segments 71 and 72 intended to contact the peripheral edge 5c of the eyeglass 5 on edge portions which are oriented perpendicular to each other. Graduated rules 73 and 74 may be provided for setting the segments 71 and 72. An additional setting device 75 and diameter rule 76 may be optionally provided for making the eyeglass positioning easier based on the diameter value of the eyeglass. Once the actual diameter value of the eyeglass 5 is selected appropriately by using the setting device 75 and rule 76, the setting of the segment 71 allows adjusting the distance between the measurement location and the eyeglass peripheral edge 5c. The segment 72 is then put backwards against the stop piece 77. Selecting at first the actual value of the eyeglass diameter with the setting device 75 allows that the measurement location can be selected with reference to a center point of the eyeglass 5. It is thus possible to select the measurement location within the eyeglass face 5a with reference to either the eyeglass center or its peripheral edge 5c.

A method is now described for measuring the reflection of the eyeglass 5 using the apparatus 100. First, the light delivery head 3 and the light collecting head 8 are set according to the desired value of the incidence angle α. A measurement wavelength window is also selected. Preferably, this wavelength window is very narrow so that it can be considered that the measurement is performed with monochromatic light.

A reference sample is obtained which has a spherical face with curvature value equal to the mean curvature value of the eyeglass 5. Also, the concave vs convex type of the reference sample is identical to that of the face 5a of the eyeglass 5 which is intended to be reflection-measured. The mean curvature value is equal to half of the sum of a maximum curvature value and a minimum curvature value of the eyeglass face 5a along two directions parallel to the face and perpendicular to each other. When the eyeglass 5 is of progressive addition type, the mean curvature value varies when moving the measurement location within the face 5a. So the reference sample is to be selected such that its curvature matches that of the eyeglass face 5a at the measurement location. Actually, it is not necessary that the curvature value of the reference sample exactly equals the mean curvature value of the eyeglass face 5a. It is sufficient that both values are close, for example with a difference of less than 1 diopter, preferably less than 0.5 diopter. For allowing measurements using the invention method for any eyeglass, a series of reference samples may be provided, with respective curvatures or curvature radii varying incrementally, for example with a 0.25 or 0.5 diopter increment in curvature. Typically, the curvature radius may vary from 70 to 160 mm for concave reference samples, and from 80 to 760 mm for convex reference samples. The back face of the reference samples may be blackened, or the material of the reference sample may be light-absorbing for suppressing unwanted reflection of the light beam at the back face.

The reflection value $R_1$ for the reference sample is known for the values selected for the incidence angle and the wavelength, either because it has been measured using another method, or because it can be read from a supplied table, or it can be calculated from the optical refractive index of the material of the reference sample. For example, this material may be crown glass BK7.

The reference sample is inserted between the upper part 4 and the lower part 6 of the sample support, and a reflection measurement is performed. This leads to an intensity value $I_1$ as detected by the sensor 12.

Then the reference sample is replaced with the eyeglass 5 in the sample support, and the reflection measurement leads to an intensity value $I_2$ detected by the sensor 12.

The reflection value of the eyeglass face 5a may then be calculated as $R_1 \times I_2/I_1$. Other value combination may be used alternatively, in case the sensing signal output by the sensor 12 is not proportional to the light intensity.

The invention can be applied to measuring residual reflection for eyeglasses each provided with an antireflecting coating on the measured faces. To this purpose, the incidence angle may be set to less than or equal to 17°, for example 15°, and the measurement wavelength may be varied from 380 nm (nanometer) to 780 nm.

Another application of the invention deals with measuring the reflection of UV radiations on the back face of an eyeglass, near its peripheral edge, for example for quantifying the amount of UV-radiations which could originate from behind the eyeglass wearer, impinge on the eyeglass back face at the temporal side and then enter into the wearer's eye. For this other application, the incidence angle may be set to 30° or 45°, and the measurement wavelength may be varied from 280 nm to 380 nm.

The invention claimed is:
1. A support adapted for performing reflection measurements on an ophthalmic eyeglass, comprising:
an upper part, comprising an upper base element and three first contact portions arranged rigidly on a lower end of the upper base element so as to produce respectively three first point-contacts with a first face of the eyeglass at respective reference locations which are fixedly defined with respect to the upper part;
a lower part, comprising a lower base element and three second contact portions each mounted on the lower base element so as to extend from an upper end of said lower base element up to respective variable distances beyond said upper end of the lower base element, and capable of providing three second point-contacts; and
means for retaining the upper and the lower parts with the respective lower and upper ends facing one another, while pressing the second contact portions towards the upper part so that the eyeglass is held between the first contact portions and said second contact portions, with the three second point-contacts located in a second face of the eyeglass opposed to the first face
the upper base element having recesses provided in opposed side faces of said upper base element, so that a light beam propagating in one of the recesses impinges on the first face of the eyeglass at a measurement location situated between the three first point-contacts, and a reflection direction of the light beam from the measurement location in the eyeglass first face runs through the other one of the recesses and exits from said other recess.

2. The support according to claim 1, wherein the lower and upper parts are oriented about an axis extending from the lower end of the upper base element towards the upper end of the lower base element, so that the three first point-contacts are respectively in line with the three second point-contacts along directions parallel to the axis.

3. The support according to claim 2, wherein the recesses in the opposed side faces of the upper base element are designed so that an incidence angle between a propagation direction of the impinging light beam and a direction perpendicular to a plane containing the three first point-contacts, is comprised between 15° and 45° included.

4. The support according to claim 2, wherein the lower base element has a clearing recess provided in a side face of said lower base element, so that a portion of the light beam transmitted through the eyeglass held between the first contact portions and the second contact portions, propagates through the clearing recess after exiting at the second face of said eyeglass.

5. The support according to claim 2, wherein the three first contact portions are arranged at the lower end of the upper base element so that the three first point-contacts form an equilateral triangle.

6. The support according to claim 2, wherein the means for retaining the upper and lower parts comprise a lift system suitable for moving the lower part towards the upper part until the eyeglass is pinch-held between the three first contact portions and the three second contact portions, while limiting a pressure of said three first contact portions onto the first face of the eyeglass, and of said three second contact portions onto the second face of the eyeglass.

7. The support according to claim 1, wherein the recesses in the opposed side faces of the upper base element are designed so that an incidence angle between a propagation direction of the impinging light beam and a direction perpendicular to a plane containing the three first point-contacts, is comprised between 15° and 45° included.

8. The support according to claim 1, wherein the lower base element has a clearing recess provided in a side face of said lower base element, so that a portion of the light beam transmitted through the eyeglass held between the first contact portions and the second contact portions, propagates through the clearing recess after exiting at the second face of said eyeglass.

9. The support according to claim 1, wherein the three first contact portions are arranged at the lower end of the upper base element so that the three first point-contacts form an equilateral triangle.

10. The support according to claim 1, wherein the means for retaining the upper and lower parts comprise a lift system suitable for moving the lower part towards the upper part until the eyeglass is pinch-held between the three first contact portions and the three second contact portions, while limiting a pressure of said three first contact portions onto the first face of the eyeglass, and of said three second contact portions onto the second face of the eyeglass.

11. A reflection measurement apparatus comprising a support according to claim 1, and further comprising a light source and a light intensity sensor, and wherein a light delivery port is connected to the means for retaining the upper and lower parts so that a light beam produced by the light source exits through the light delivery port, then propagates through one of the recesses of the upper base element and impinges onto the first face of the eyeglass,
a light collecting port is also connected to said means for retaining the upper and lower parts so that the beam produced by the light source and reflected by the first face of the eyeglass runs through the other recess of the upper base element, then enters into the light collecting port and reaches the light intensity sensor.

12. The apparatus according to claim 11, wherein the light source is adapted for outputting the light beam with radiation continuously distributed over the wavelength range from 280 nm to 780 nm, and the apparatus further comprises a radiation selector arranged so that the light intensity sensor senses radiations limitedly within a wavelength window selected between 280 nm and 780 nm.

13. The apparatus according to claim 12, comprising an angle setting system adapted for moving both the light delivery port and the light collecting port so that an incidence angle between a propagation direction of the impinging light beam and a direction perpendicular to a plane containing the three first point-contacts, and also between said perpendicular direction and a propagation direction of the light beam as reflected by the first face of the eyeglass, is set to a target value selected within an angle range extending from a lower angle value less than or equal to 17°, up to an upper angle value higher than or equal to 45°.

14. The apparatus according to claim 12, further comprising a transverse positioning system adapted for setting a transverse position of the eyeglass along directions perpendicular to an axis extending from the lower end of the upper base element towards the upper end of the lower base element, so that the measurement location is selected within the first face of the eyeglass by the setting of the eyeglass transverse position, said transverse positioning system comprising at least one abutment segment arranged for contacting a peripheral edge of the eyeglass, and adjustable in separating distance from the measurement location.

15. A method for performing a reflection measurement on an eyeglass, using an apparatus in accordance with claim 12, and comprising the following steps:
a) providing a set of reference samples having respective measurement faces of spherical shapes with known curvature values, each reference sample having a known reflection value and being designed so that a back face of said reference sample does not contribute to reflecting radiation;
b) obtaining the eyeglass to be reflection-measured, and obtaining a mean curvature value of a face of said eyeglass where the reflection measurement is to be performed;
c) selecting one of the reference samples, so that the curvature value of the selected reference sample matches the mean curvature value of the eyeglass face to be reflection-measured;
d) using the apparatus with the selected reference sample held in the support, performing a first reflection measurement and obtaining a first intensity value from the light intensity sensor;
e) replacing the reference sample with the eyeglass in the support, and performing a second reflection measurement and obtaining a second intensity value from the light intensity sensor; and
f) obtaining a result for the reflection value of the eyeglass face by combining the reflection value of the reference sample selected in step c), with the first and second intensity values respectively obtained in steps d) and e);

wherein the known reflection values of the reference samples and the measurements performed in steps d) and e) relate to a same incidence angle value and a same wavelength window.

16. The apparatus according to claim 11, comprising an angle setting system adapted for moving both the light delivery port and the light collecting port so that an incidence angle between a propagation direction of the impinging light beam and a direction perpendicular to a plane containing the three first point-contacts, and also between said perpendicular direction and a propagation direction of the light beam as reflected by the first face of the eyeglass, is set to a target value selected within an angle range extending from a lower angle value less than or equal to 17°, up to an upper angle value higher than or equal to 45°.

17. The apparatus according to claim 16, further comprising a transverse positioning system adapted for setting a transverse position of the eyeglass along directions perpendicular to an axis extending from the lower end of the upper base element towards the upper end of the lower base element, so that the measurement location is selected within the first face of the eyeglass by the setting of the eyeglass transverse position, said transverse positioning system comprising at least one abutment segment arranged for contacting a peripheral edge of the eyeglass, and adjustable in separating distance from the measurement location.

18. A method for performing a reflection measurement on an eyeglass, using an apparatus in accordance with claim 16, and comprising the following steps:
  a) providing a set of reference samples having respective measurement faces of spherical shapes with known curvature values, each reference sample having a known reflection value and being designed so that a back face of said reference sample does not contribute to reflecting radiation;
  b) obtaining the eyeglass to be reflection-measured, and obtaining a mean curvature value of a face of said eyeglass where the reflection measurement is to be performed;
  c) selecting one of the reference samples, so that the curvature value of the selected reference sample matches the mean curvature value of the eyeglass face to be reflection-measured;
  d) using the apparatus with the selected reference sample held in the support, performing a first reflection measurement and obtaining a first intensity value from the light intensity sensor;
  e) replacing the reference sample with the eyeglass in the support, and performing a second reflection measurement and obtaining a second intensity value from the light intensity sensor; and
  f) obtaining a result for the reflection value of the eyeglass face by combining the reflection value of the reference sample selected in step c), with the first and second intensity values respectively obtained in steps d) and e);
  wherein the known reflection values of the reference samples and the measurements performed in steps d) and e) relate to a same incidence angle value and a same wavelength window.

19. The apparatus according to claim 11, further comprising a transverse positioning system adapted for setting a transverse position of the eyeglass along directions perpendicular to an axis extending from the lower end of the upper base element towards the upper end of the lower base element, so that the measurement location is selected within the first face of the eyeglass by the setting of the eyeglass transverse position, said transverse positioning system comprising at least one abutment segment arranged for contacting a peripheral edge of the eyeglass, and adjustable in separating distance from the measurement location.

20. A method for performing a reflection measurement on an eyeglass, using an apparatus in accordance with claim 11, and comprising the following steps:
  a) providing a set of reference samples having respective measurement faces of spherical shapes with known curvature values, each reference sample having a known reflection value and being designed so that a back face of said reference sample does not contribute to reflecting radiation;
  b) obtaining the eyeglass to be reflection-measured, and obtaining a mean curvature value of a face of said eyeglass where the reflection measurement is to be performed;
  c) selecting one of the reference samples, so that the curvature value of the selected reference sample matches the mean curvature value of the eyeglass face to be reflection-measured;
  d) using the apparatus with the selected reference sample held in the support, performing a first reflection measurement and obtaining a first intensity value from the light intensity sensor;
  e) replacing the reference sample with the eyeglass in the support, and performing a second reflection measurement and obtaining a second intensity value from the light intensity sensor; and
  f) obtaining a result for the reflection value of the eyeglass face by combining the reflection value of the reference sample selected in step c), with the first and second intensity values respectively obtained in steps d) and e);
  wherein the known reflection values of the reference samples and the measurements performed in steps d) and e) relate to a same incidence angle value and a same wavelength window.

* * * * *